United States Patent [19]

Callahan et al.

[11] Patent Number: 4,615,703
[45] Date of Patent: Oct. 7, 1986

[54] INTRAOCULAR LENS DELIVERY SYSTEM

[75] Inventors: Wayne B. Callahan, Milton; Timothy B. Cowen; Harold O. Koch, both of Barboursville, all of W. Va.

[73] Assignee: Cilco, Inc., Huntington, W. Va.

[21] Appl. No.: 516,340

[22] Filed: Jul. 22, 1983
(Under 37 CFR 1.47)

[51] Int. Cl.$^4$ .......... A61F 2/16; A61B 17/00; B65D 81/24
[52] U.S. Cl. .................. 623/6; 128/303 R; 206/5.1; 206/210
[58] Field of Search .......... 3/13; 128/303 R; 206/5.1, 210; 623/6

[56] References Cited

U.S. PATENT DOCUMENTS

| | | | |
|---|---|---|---|
| 4,173,281 | 11/1979 | Trought | 206/210 X |
| 4,240,163 | 12/1980 | Galin | 3/13 |
| 4,251,887 | 2/1981 | Anis | 3/13 |
| 4,269,307 | 5/1981 | La Haye | 206/5.1 |
| 4,435,855 | 3/1984 | Pannu | 3/13 |
| 4,468,820 | 9/1984 | Uhler et al. | 3/13 |

Primary Examiner—Ronald L. Frinks
Attorney, Agent, or Firm—Lyon & Lyon

[57] ABSTRACT

A system for collapsing the lens loops of an intraocular lens in preparation for insertion of the lens into a human eye and forming and maintaining the lens loops in a collapsed position during the lens insertion operation. The system includes an apparatus for mating the intraocular lens with an incapsulating structure such as a wafer fabricated from viscoelastic material. The device is designed in a manner which causes the lens loops of the intraocular lens to collapse as the lens is inserted into the incapsulating structure during the mating process. In a preferred embodiment, the device may comprise a rotor element mounted on a baseplate for supporting the intraocular lens beneath the incapsulating structure, whereby the lens can be rotated or "dialed" into the incapsulating structure.

1 Claim, 4 Drawing Figures

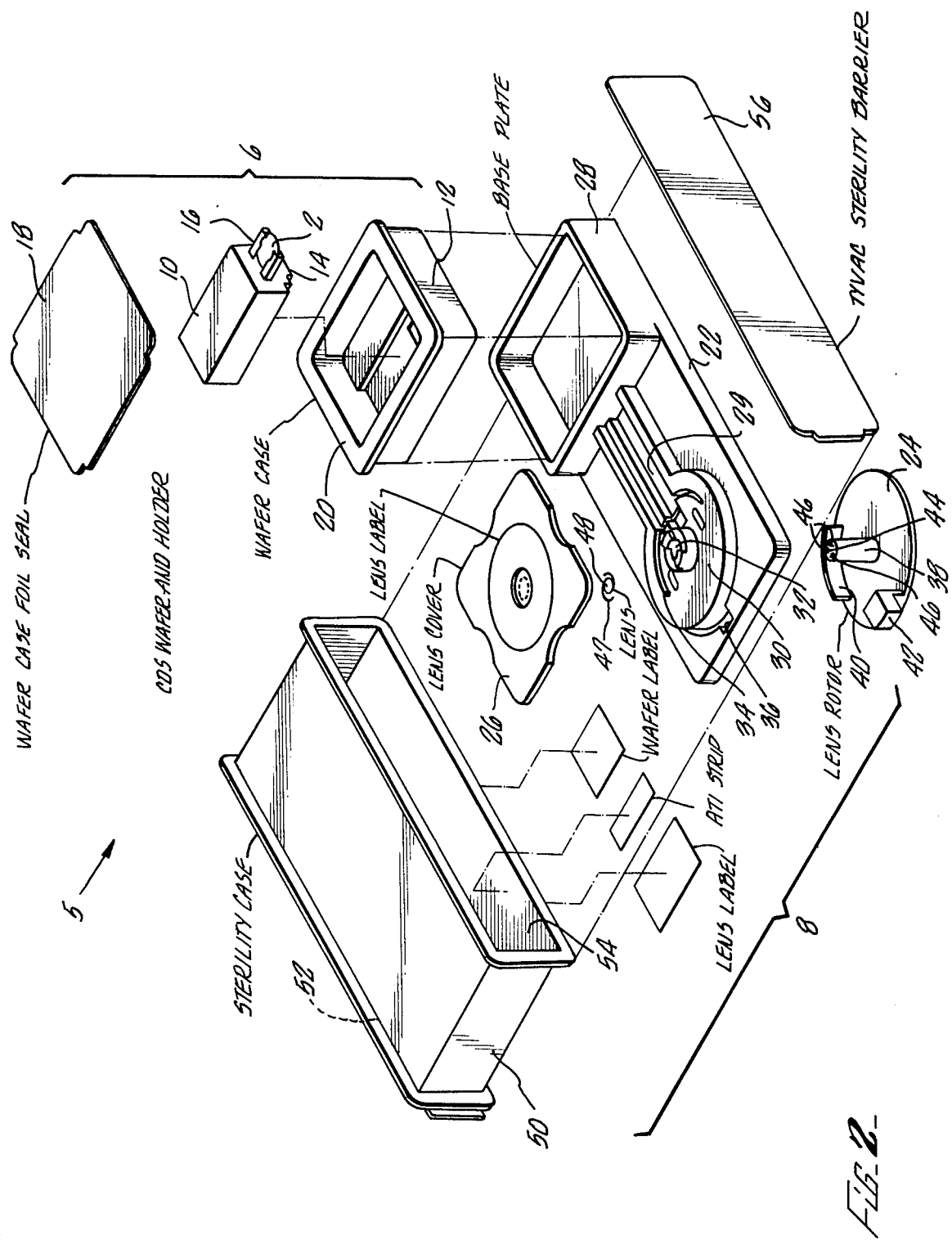

INTRAOCULAR LENS DELIVERY SYSTEM

BACKGROUND OF INVENTION

The invention relates to the use of a viscoelastic material such as sodium chondroitin sulfate that is dried into any of several shapes, for the purposes of:

1. Providing a vehicle for the insertion of an intraocular lens into either the anterior or posterior chamber of a human eye following cataract extraction.

2. Collapsing the loops of an anterior chamber or posterior chamber intraocular lens immediately prior to surgical implantation to facilitate insertion of the lens into the anterior chamber or through the iris into the posterior chamber without the undue manipulation required by the use of these lenses currently.

3. Releasing the loops of posterior chamber lenses, after insertion, slowly and uniformly, by the dissolution of the viscoelastic material, allowing the lens to assume its normal shape upon expansion, and requiring minimum surgical manipulation for centration and placement.

4. Protecting the corneal endothelium, and other sensitive ocular tissues, from damage caused by touching of the lens to these tissues during the surgical procedure, or by surgical instruments used during the surgical procedure.

The invention also relates to the processes for obtaining and manufacturing such a product, and the method of packaging the product, which is unique in that:

1. The dried viscoelastic material, henceforth called a "wafer", is packaged together with the intraocular lens in an unloaded position.

2. Upon opening of the sterility barrier by the surgical personnel, the wafer holder loads the lens into the wafer without direct touching of the wafer or the lens by any foreign object, and without undue stress being applied to the lens.

BRIEF DESCRIPTION OF THE DRAWINGS

The various features, objects and advantages of the present invention can be better understood in conjunction with the accompanying drawings, where:

FIG. 2 is an exploded view of the system whereby an intraocular lens is loaded into the wafer of FIGS. 1A-1C in preparation for insertion of the lens/wafer assembly into either the anterior or posterior chamber of a human eye.

BEST MODE FOR CARRYING OUT THE INVENTION

Figure 1B:
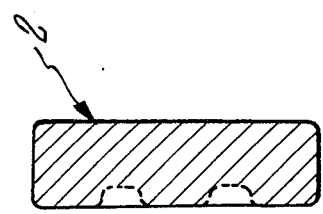
FIGS. 1A, 1B, and 1C respectively illustrate top, side, and front elevation views of a chondroitin sulfate wafer.
Figure 1A:
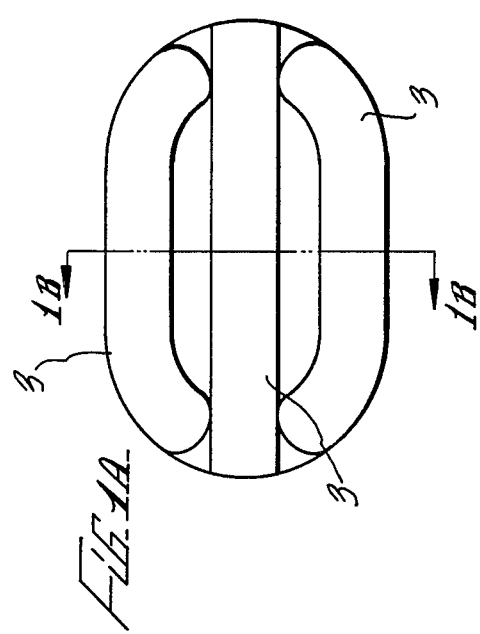
Figure 1C:
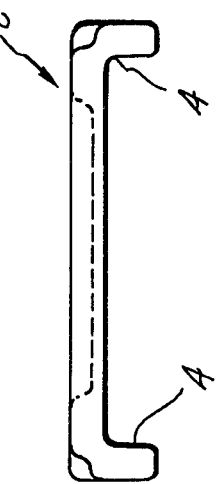

A wafer 2 is manufactured by molding a viscoelastic material such as chondroitin sulfate into a shape such as that depicted in FIGS. 1A-1C and drying the material under controlled conditions. The wafer should have at least one rib 3 and a pair of overhanging sections 4 against which the loops of the intraocular lens will rest. When so manufactured, the wafer is:

(a) The appropriate size for insertion into either the anterior or posterior chamber of a human eye as specified (approximately 10 mm × 7 mm).

(b) Designed to collapse the loops of a posterior chamber lens to a size small enough to allow insertion through the iris into the posterior chamber without damaging the iris.

(c) Designed to dissolve within 0.25 to 10.0 minutes, releasing the loops of a posterior chamber lens or the feet of an anterior chamber lens.

Wafer 2 is further described in co-pending application Ser. No. 516,341 filed on July 22, 1983, now abandoned.

The wafer delivery system 5, which can be seen to best advantage in FIG. 2, comprises a wafer package indicated generally at 6 and a lens package indicated generally at 8. Wafer package 6 includes a wafer holder 10 and a wafer case 12. A longitudinal key 14 extends from the bottom of wafer holder 10 and a projection 16 is formed on the side of the wafer holder to receive and support wafer 2. The wafer holder is placed in the wafer case 12 and a foil seal 18 is applied to the upper lip 20 of the wafer case to complete assembly of the wafer package. The wafer package may thereafter be radiation sterilized.

Lens package 8 includes a baseplate 22, a lens rotor 24, and a lens cover 26. One end of baseplate 22 is formed with raised walls 28 adapted to the shape of the wafer case 12 of wafer package 6. The other end of baseplate 22 contains a depression or track 29 leading to a raised section 30 having a cylindrical opening 32 formed in the center thereof. Track 29 conforms to the shape of the key 14 on the bottom of wafer holder 10. A slot 34 formed in one end of raised portion 30 assists in guiding the rotation of lens rotor 24 as will be described shortly. A keyway 36 is disposed about the circumference of raised portion 30 to assist in aligning the lens rotor 24, as will also be described shortly.

Lens rotor 24 is formed within a spindle 38 shaped to fit the central opening 32 of raised portion 30. When assembling the lens package, spindle 38 is fitted through central opening 32. Simultaneously, slot 34 in raised portion 30 receives a curved wall 40 formed on lens rotor 24 while a key 42 projecting from lens rotor 24 passes through keyway 36 in baseplate 22. Curved wall 40 and key 42 serve to maintain the position of lens rotor 24 relative to raised portion 30 as the lens rotor rotates about spindle 38. The top face 44 of spindle 38 on lens rotor 24 has a series of cam rings 46 which hold the loops 47 of intraocular lens 48 in place in an initially uncompressed condition. These cam rings are positioned to accept numerous lens styles. The initial position of the lens rotor relative to baseplate 22 will depend on whether the lens is to be "dialed" into the wafer in a clockwise or counterclockwise direction. Lens cover 26 is then placed over the lens and locked to baseplate 22.

Final packaging of the wafer delivery system proceeds as follows. The lens cover is imprinted with any information required by the user. The assembled baseplate, lens rotor, lens and lens cover are cleaned and dried and the radiation sterilized wafer case 12 is inserted inside raised walls 28 on baseplate 22. The combined wafer and lens packages are finally placed in a hollow sterility case 50, one end of which is open and the other end 54 of which has been presealed with a Tyvek seal (not shown). When this latter assembly step is complete, a second Tyvek sterility barrier 56 is used to seal the remaining opening of the sterility case and the wafer delivery system is complete. ETP sterilization may be subsequently performed on the system if desired.

ACTIVATION METHODOLOGY

1. Upon receipt by the physician, the sterility barrier will be removed aseptically in the operating room.
2. The foil seal is first removed followed by the lens cover cap.
3. Remove the wafer holder and insert it into the track of the base plate with the wafer end pointed toward the lens rotor.
4. Slide the wafer holder to the stop and gently activate the lens rotor by turning in either a clockwise or counterclockwise direction ninety (90) degrees to load the posterior chamber lens. As the lens rotor is turned, the loops of the posterior lens will slowly be compressed against the sides of the wafer until the lens is completely held by the wafer.

NOTE: No activation of the cam ring is required or possible with the anterior chamber lenses.

5. The system is activated. To implement, simply take up the wafer holder with the loaded lens and grasp the wafer in its designated area with a forcep and remove the wafer and lens from the holder.

INTENDED SURGICAL USE OF THE INVENTION

The wafer will be designed for certain styles of either anterior chamber or posterior chamber intraocular lenses.

1. The anterior chamber lens will be slid into a wafer, whereupon, the surgeon will grasp the designated end of the wafer, which now holds the lens with its anterior side covered, with forceps. This wafer/lens combination will be inserted into the anterior chamber, after cataract extraction. The wafer will be positioned in the same manner as described for anterior chamber lens surgical procedures. Upon dissolution of the wafer, the surgeon can perform any minor adjustments necessary for final placement of the lens. The dissolving sodium chondroitin sulfate will also act as a viscoelastic agent in maintaining the corneal dome, and protection of intraocular tissues.

2. The posterior chamber lens will be dialed into the wafer, thereby compressing the lens loops to a designated size. This will be accomplished immediately prior to implantation by movement of the components of the combined lens and wafer package, and will not require the touch of either by any foreign object. The surgeon will then grasp the designated end of the wafer, which now holds the lens with its anterior side covered, and insert it through the corneal incision, through the iris, and into the posterior chamber. The wafer will be of such dimension that manual dilation of the iris will not be necessary to achieve insertion. As the wafer dissolves, within three minutes, the loops of the lens will expand, and open to their full dimension. This will provide centration and placement of the lens as described in currently accepted surgical protocol. The surgeon may, at this time, effect any minor adjustments in placement as necessary. The dissolving sodium chondroitin sulfate will also act as an viscoelastic agent, and provide protection of the ocular tissue.

What is claimed is:

1. A delivery system for placing an intraocular lens having compressible lens loops into a wafer structure having overhanging sections designed to hold the lens loops in compressed position, said system comprising:
   a holder means for supporting the wafer;
   a baseplate structure having a track means formed therein to receive said holder means and to guide said holder means from a first position to a second position; and
   a rotor means mounted on said baseplate structure for supporting the intraocular lens beneath the wafer structure when said holder means is moved from said first to said second positions such that the loops of the lens remain in an uncompressed condition and for rotating in a predetermined direction relative to said baseplate structure while said holder means remains in said second position such that the loops of the intraocular lens are compressed against the overhanging sections of the wafer structure.

* * * * *